US012779090B2

(12) United States Patent
Sakai et al.

(10) Patent No.: US 12,779,090 B2
(45) Date of Patent: Nov. 3, 2026

(54) GEL MATERIAL FOR TREATING TENDON OR LIGAMENT

(71) Applicants: The University of Tokyo, Tokyo (JP); GELLYCLE CO., LTD., Tokyo (JP)

(72) Inventors: Takamasa Sakai, Tokyo (JP); Taku Saito, Tokyo (JP); Yasuhide Iwanaga, Tokyo (JP); Sakae Tanaka, Tokyo (JP); Kosuke Masui, Tokyo (JP); Shinichi Narita, Tokyo (JP)

(73) Assignees: THE UNIVERSITY OF TOKYO, Tokyo (JP); GELLYCLE CO., LTD., Tokyo (JP)

( * ) Notice: Subject to any disclaimer, the term of this patent is extended or adjusted under 35 U.S.C. 154(b) by 583 days.

(21) Appl. No.: 18/005,919

(22) PCT Filed: Jul. 13, 2021

(86) PCT No.: PCT/JP2021/026352
§ 371 (c)(1),
(2) Date: Jan. 18, 2023

(87) PCT Pub. No.: WO2022/019182
PCT Pub. Date: Jan. 27, 2022

(65) Prior Publication Data

US 2023/0330304 A1 Oct. 19, 2023

(30) Foreign Application Priority Data

Jul. 22, 2020 (JP) ................................. 2020-125055

(51) Int. Cl.
*A61L 27/52* (2006.01)
*A61L 27/26* (2006.01)

(52) U.S. Cl.
CPC ............... *A61L 27/52* (2013.01); *A61L 27/26* (2013.01); *A61L 2430/10* (2013.01)

(58) Field of Classification Search
CPC ....... A61L 27/52; A61L 27/26; A61L 2430/10
See application file for complete search history.

(56) References Cited

U.S. PATENT DOCUMENTS

2011/0150821 A1* 6/2011 Daniloff .................. A61P 19/04 424/78.36
2012/0122949 A1 5/2012 Tei et al.
2018/0030205 A1 2/2018 Sakai et al.
2019/0015559 A1 1/2019 Sakai et al.
2020/0054786 A1* 2/2020 Liu ........................ A61K 8/736
2021/0155799 A1 5/2021 Sakai et al.

FOREIGN PATENT DOCUMENTS

CN 103937014 A 7/2014
CN 104307052 A 1/2015
CN 107428930 A 12/2017
WO 2007083522 A1 7/2007
WO 2010/070775 A1 6/2010
WO 2017/119296 A1 7/2017
WO 2020/027016 A1 2/2020

OTHER PUBLICATIONS

Chinese Office Action of related CN 202180060328.0, dated Oct. 25, 2024, including translation. [12 pages].
Chinese Office Action of related CN 202180060328.0, dated May 14, 2025, including translation. [10 pages].
Veronesi, Francesca et al. “Evaluation of a new collagen-based medical device (ElastiCo) for the treatment of acute Achilles tendon injury and prevention of peritendinous adhesions: An in vitro biocompatibility and in vivo investigation”, J. Tissue Eng. Regen. Med., 2020, vol. 14, No. 8, pp. 1113-1125.
Ishiyama, Noriyuki et al. “The prevention of peritendinous adhesions by a phospholipid polymer hydrogel formed in situ by spontaneous intermolecular interactions”, Biomaterials, 2010, vol. 31, pp. 4009-4016.
Ishiyama, Noriyuki et al. “Reduction of Peritendinous Adhesions by Hydrogel Containing Biocompatible Phospholipid Polymer MPG for Tendon Repair”, J Bone Joint Surg Am, 2011, vol. 93, pp. 142-149.
Kobayashi, Masanori et al. “Development of the Shields for Tendon Injury Repair Using Polyvinyl Alcohol Hydrogel (PVA H)”, Journal of Biomedical Materials Research, 2001, vol. 58, No. 4, pp. 344-351.
Best et.al. “Scleraxis lineage cells contribute to organized bridging tissue during tendon healing and identify a subpopulation of resident tendon cells”: The FASEB Journal, 2019, vol. 33: 8578-8587.
International Search Report and Written Opinion of PCT/JP2021/026352, mailed Sep. 14, 2021.
Matsunaga et al., Macromolecules, vol. 42, No. 4, pp. 1344-1351, 2009.

* cited by examiner

*Primary Examiner* — Sean M Basquill
(74) *Attorney, Agent, or Firm* — Leason Ellis LLP

(57) ABSTRACT

To provide a method for suppressing the entry of scar tissue in the treatment of a tendon or ligament, promoting healing by intratendinous cells, and efficiently restoring the original function of the tendon.

A gel material including a polymer gel for suppressing expression of type III collagen in the treatment of an injured or ruptured tendon or ligament, in which the polymer gel is a hydrogel having a three-dimensional network structure formed by crosslinking of hydrophilic polymers, and has a polymer content of from 1 to 5% by weight and an elastic modulus of from 100 to 10000 Pa.

3 Claims, 1 Drawing Sheet

GEL MATERIAL FOR TREATING TENDON OR LIGAMENT

TECHNICAL FIELD

The present invention relates to a gel material suitable for treatment of a tendon or ligament, and a method for treating a tendon or ligament using the gel material.

BACKGROUND ART

In general, no effective treatment for tendon and ligament injuries has been established to date. On the other hand, surgical treatment, such as suture for tendon rupture and ligament reconstruction for ligament rupture, is the treatment of choice, while conservative treatment is chosen for partial injuries.

However, in both treatments, the healing process of tendon ligament is mixed with healing by scar tissue composed of extra-tendon cells (fibroblasts and inflammatory cells), which inhibits healing of the tendon or ligament itself (for example, Non Patent Literature 1). Therefore, the strength of the cured tendon ligament decreases to the same level as that of the scar tissue, and thus the tendon cannot exert its original function. This leads to re-rupture after surgery and hinders return to sports, reducing the quality of life (QOL) of many patients.

CITATION LIST

Non Patent Literature

Non Patent Literature 1: Best et. al, The FASEB Journal, vol. 33, July 2019

SUMMARY OF INVENTION

Technical Problem

Therefore, an object of the present invention is to provide a method for suppressing the entry of scar tissue in the treatment of a tendon or ligament, promoting healing by intratendinous cells, and efficiently restoring the original function of the tendon.

Solution to Problem

As a result of intensive studies to solve the above problems, the present inventors have found that coating the area around an injured or ruptured tendon or ligament with a hydrogel, which has a three-dimensional network structure formed by intermolecular crosslinking of hydrophilic polymers, suppresses the entry of scar tissue composed mainly of type III collagen, and efficiently achieves endogenous healing by intratendinous cells, thereby completing the present invention.

That is, in one aspect, the present invention relates to a gel material suitable for the treatment of an injured or ruptured tendon or ligament, and more specifically provides the followings.

<1> A gel material including a polymer gel for suppressing expression of type III collagen in a treatment of an injured or ruptured tendon or ligament, in which the polymer gel is a hydrogel having a structure in which a hydrophilic polymer is crosslinked to form a three-dimensional network structure, and has a polymer content of from 2 to 5% by weight and an elastic modulus of from 100 to 10000 Pa.

<2> The gel material according to <1>, in which the hydrophilic polymer has a polyether or polyvinyl backbone.

<3> The gel material according to <1> or <2>, in which the hydrophilic polymer is bi-, tri-, or tetra-branched polyethylene glycol.

<4> The gel material according to any one of <1> to <3>, in which the hydrophilic polymer includes a first polymer unit having one or more nucleophilic functional groups on a side chain or at an end and a second polymer unit having one or more electrophilic functional groups on a side chain or at an end.

<5> The gel material according to <4>, in which the nucleophilic functional group is selected from the group consisting of a thiol group and an amino group, and the electrophilic functional group is selected from the group consisting of a maleimidyl group, an N-hydroxy-succinimidyl (NHS) group, a sulfosuccinimidyl group, a phthalimidyl group, an imidazoyl group, an acryloyl group, a nitrophenyl group, and $—CO_2PhNO_2$.

<6> The gel material according to any one of <1> to <5>, which is used for coating a tendon or ligament after suture of the tendon or ligament.

<7> The gel material according to <6>, which is able to suppress expression of type III collagen and maintain expression of type I collagen by coating the tendon or ligament.

<8> A kit for preparing the gel material according to any one of <1> to <7>, which includes two or more solutions each containing a hydrophilic polymer.

In another aspect, the present invention relates to the treatment of a tendon or ligament using the gel material, and more specifically provides the followings.

<9> A method for treating an injured or ruptured tendon or ligament, including coating an area around the tendon or ligament after suture with the gel material according to any one of <1> to <7>.

<10> A method for suppressing expression of type III collagen in a tendon or ligament, including coating an area around the tendon or ligament after suture with the gel material according to any one of <1> to <7>.

<11> A method for treating an injured or ruptured tendon or ligament, including the steps of: preparing a polymer solution A containing a first hydrophilic polymer having one or more nucleophilic functional groups on a side chain or at an end, and a polymer solution B containing a second hydrophilic polymer having one or more electrophilic functional groups on a side chain or at an end; applying the polymer solutions A and B to an area around the tendon or ligament after suture to form a polymer gel having a structure in which the hydrophilic polymers are crosslinked to form a three-dimensional network structure, thereby coating the area around the tendon or ligament; and suppressing expression of type III collagen in the tendon or ligament by the coating.

<12> The treatment method according to <11>, in which the polymer gel has a polymer content of from 1 to 5% by weight and an elastic modulus of from 100 to 10000 Pa.

<13> The treatment method according to <11> or <12>, in which the first and second hydrophilic polymers have a polyether or polyvinyl backbone.

<14> The treatment method according to any one of <11> to <13>, in which the first and second hydrophilic polymers are bi-, tri-, or tetra-branched polyethylene glycols.

<15> The treatment method according to any one of <11> to <14>, in which the nucleophilic functional group is selected from the group consisting of a thiol group and an amino group, and the electrophilic functional group is selected from the group consisting of a maleimidyl group, an N-hydroxy-succinimidyl (NHS) group, a sulfosuccinimidyl group, a phthalimidyl group, an imidazoyl group, an acryloyl group, a nitrophenyl group, an isothiocyanate group, an aldehyde group, an iodoacetamide group, a vinyl sulfone group, and $—CO_2PhNO_2$.

In a further aspect, the present invention also relates to a screening method using the gel material, and more specifically provides the following.

<16> A method for screening an agent effective for treatment of an injured or ruptured tendon or ligament, including a step of searching for and identifying a compound having activity to proliferate type I collagen in a tendon or ligament coated with the gel material according to any one of <1> to <7>.

Advantageous Effects of Invention

According to the gel material and the treatment method of the present invention, entry of inflammatory cells and fibroblasts from around the affected area can be suppressed, and entry of scar tissue containing type III collagen as a main component, which has been considered to be inevitable in the healing process of the tendon ligament, can be suppressed or eliminated. This has the effect of promoting endogenous healing based on the expression of type I collagen by intratendinous cells and efficiently restoring the original function of the tendon, which is an effect that has not been achieved by conventional methods.

DESCRIPTION OF EMBODIMENTS

Figure 1:
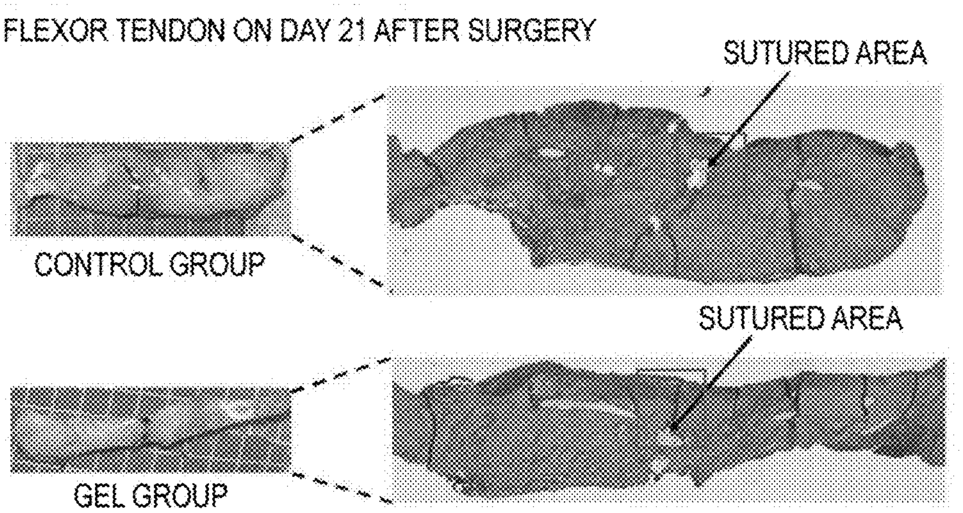
FIG. 1 shows images of a flexor tendon coated with the gel of the present invention (gel group) and a flexor tendon not coated with the gel (control group) on Day 21 after surgery.

Hereinafter, embodiments of the present invention will be described. The scope of the present invention is not limited by these descriptions, and the present invention can be implemented with modifications other than those shown in the examples below without impairing the gist of the invention.

1. Gel Material of the Present Invention

The gel material of the present invention is a gel material containing a polymer gel for suppressing the expression of type III collagen in the treatment of an injured or ruptured tendon or ligament. The polymer gel is a hydrogel having a structure in which hydrophilic polymers are crosslinked to form a three-dimensional network structure, and has a polymer content of from 1 to 5% by weight and an elastic modulus of from 100 to 10000 Pa. Here, the "elastic modulus" means a storage modulus G'.

(1-1) Hydrophilic Polymer

The hydrophilic polymers constituting the polymer gel are those that can form a hydrogel by being crosslinked, and more specifically, those that can form a network structure, especially a three-dimensional network structure, in the final gel by crosslinking the polymers with each other or through any low molecular weight compounds. The hydrophilic polymers may be any hydrophilic polymers known in the art, as long as they can form a hydrogel by gelation reaction (crosslinking reaction or the like) in an aqueous solution, and are preferably hydrophilic polymers having a polyether or polyvinyl backbone.

Typical examples of the polymer having a polyether backbone include polymer having a polyalkylene glycol backbone. Preferable examples thereof include polymers having a polyethylene glycol backbone with a plurality of branches, of these, bi-, tri-, or tetra-branched polyethylene glycols are particularly preferred. Gels composed of a tetra-branched polyethylene glycol backbone are generally known as Tetra-PEG gels, in which a network structure is constructed by an AB-type cross-end coupling reaction between two tetra-branched polymers having electrophilic functional groups such as active ester structures and nucleophilic functional groups such as amino groups at the ends (Matsunaga et al., Macromolecules, Vol. 42, No. 4, pp. 1344-1351, 2009). Tetra-PEG gels can be easily prepared in situ by simply mixing two polymer solutions, and the gelation time can be controlled by adjusting the pH and ionic strength during gel preparation. Since the gel includes PEG as a main component, it has excellent biocompatibility.

Examples of the hydrophilic polymer having a polyvinyl backbone include polyalkyl methacrylates such as polymethyl methacrylate, polyacrylates, polyvinyl alcohols, poly N-alkyl acrylamides, and polyacrylamides.

The hydrophilic polymer has a weight average molecular weight (Mw) of from $1\times10^3$ to $1\times10^5$, preferably from $5\times10^3$ to $5\times10^4$, and more preferably from $1\times10^4$ to $4\times10^4$.

In a preferred aspect, the hydrophilic polymer is a combination of a first polymer unit having one or more nucleophilic functional groups on the side chain or at the end and a second polymer unit having one or more electrophilic functional groups on the side chain or at the end. For example, the first polymer unit preferably has one or more nucleophilic functional groups on the side chain or at the end, and the second polymer unit preferably has one or more electrophilic functional groups on the side chain or at the end. The nucleophilic and electrophilic functional groups are crosslinked to form a gel having a three-dimensional network structure. The total of the nucleophilic and electrophilic functional groups is preferably 5 or more. These functional groups are more preferably present at the end.

Examples of the nucleophilic functional group present in the first and second polymer units include thiol (—SH) and amino groups. In addition, nucleophilic functional groups known to those skilled in the art may be used as appropriate. The nucleophilic functional group is preferably a —SH group. The nucleophilic functional groups may be the same or different, but are preferably the same. When the functional groups are the same, reactivity with the electrophilic functional group that forms a crosslinking bond becomes uniform, and a gel having a homogenous network structure is easily obtained.

The electrophilic functional groups present in the first and second polymer units may be active ester groups. Examples of the active ester group include a maleimidyl group, an N-hydroxy-succinimidyl (NHS) group, a sulfosuccinimidyl group, a phthalimidyl group, an imidazoyl group, an acryloyl group, a nitrophenyl group, an isothiocyanate group, an aldehyde group, an iodoacetamide group, a vinyl sulfone group, and $—CO_2PhNO_2$ (Ph represents an o-, m-, or p-phenylene group), and other active ester groups known to those skilled in the art may be used as appropriate. The electrophilic functional group is preferably a maleimidyl group. The electrophilic functional groups may be the same or different, but are preferably the same. When the functional groups are the same, reactivity with the nucleophilic functional group that forms a crosslinking bond becomes uniform, and a gel having a homogeneous network structure is easily obtained.

A preferred non-limiting specific example of the polymer unit having a nucleophilic functional group at the end is a compound represented by the following formula (I) having four polyethylene glycol backbone branches and thiol groups at the ends.

[Chemical Formula 1]

(I)

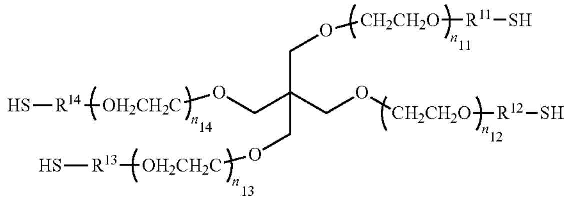

In the formula (I), $R^{11}$ to $R^{14}$ are the same or different and each represent a $C_1$-$C_7$ alkylene group, a $C_2$-$C_7$ alkenylene group, $—NH—R^{15}—$, $—CO—R^{15}—$, $—R^{16}—O\ R^{17}—$, $—R^{16}—NH—R^{17}—$, $—R^{16}—CO_2—R^{17}—$, $—R^{16}—CO_2—NH—R^{17}—$, $—R^{16}—CO—R^{17}—$, or $—R^{16}—CO—NH—R^{17}—$ wherein $R^{15}$ represents a $C_1$-$C_7$ alkylene group, $R^{16}$ represents a $C_1$-$C_3$ alkylene group, and $R^{17}$ represents a $C_1$-$C_5$ alkylene group.

The $n_{11}$ to $n_{14}$ may be the same or different from each other. The closer the values of $n_{11}$ to $n_{14}$ are, the more homogeneous the network structure and the higher the strength. Therefore, in order to obtain a high-strength gel, they are preferably the same. If the values of $n_{11}$ to $n_{14}$ are too high, the gel strength is weak, and when the values of $n_{11}$ to $n_{14}$ are too low, the gel is difficult to form due to steric hindrance of the compound. Therefore, examples of $n_{11}$ to $n_{14}$ include integer values of from 25 to 250, of which 35 to 180 is preferred, 50 to 115 is even more preferred, and 50 to 60 is particularly preferred. The weight average molecular weight (Mw) thereof is from $1\times10^3$ to $1\times10^5$, preferably from $5\times10^3$ to $5\times10^4$, and more preferably from $1\times10^4$ to $4\times10^4$.

In the above formula (I), $R^{11}$ to $R^{14}$ are linker moieties connecting the functional groups and the core portion. $R^{11}$ to $R^{14}$ may be the same or different, but are preferably the same in order to produce a high-strength gel having a homogeneous network structure. $R^{11}$ to $R^{14}$ each represent a $C_1$-$C_7$ alkylene group, a $C_2$-$C_7$ alkenylene group, $—NH—R^{15}—$, $—CO—R^{15}—$, $—R^{16}—O—R^{17}—$, $—R^{16}—NH—R^{17}—$, $—R^{16}—CO_2—R^{17}—$, $—R^{16}—CO_2—NH—R^{17}—$, $R^{16}—CO—R^{17}—$, or $—R^{16}—CO—NH—R^{17}—$. Wherein $R^{15}$ represents a $C_1$-$C_7$ alkylene group. $R_{16}$ represents a $C_1$-$C_3$ alkylene group. $R^{17}$ represents a $C_1$-$C_5$ alkylene group.

Here, the "$C_1$-$C_7$ alkylene group" means an alkylene group having 1 to 7 carbon atoms which may be branched, and means a linear $C_1$ to $C_7$ alkylene group or a $C_2$-$C_7$ alkylene group having one or more branches (the number of carbon atoms including the branch is from 2 to 7). Examples of the $C_1$-$C_7$ alkylene group are methylene, ethylene, propylene, and butylene groups. Examples of the $C_1$-$C_7$ alkylene group include $—CH_2—$, $—(CH_2)_2—$, $—(CH_2)_3—$, $—CH(CH_3)—$, $—(CH_2)_3—$, $—(CH(CH_3))_2—$, $—(CH_2)_2—CH(CH_3)—$, $—(CH_2)_3—CH(CH_3)—$, $—(CH_2)_2—CH(C_2H_5)—$, $—(CH_2)_6—$, $—(CH_2)_2—C(C_2H_5)_2—$, and $—(CH_2)_3C(CH_3)_2CH_2—$.

The "$C_2$-$C_7$ alkenylene group" is a linear or branched alkenylene group having 2 to 7 carbon atoms with one or more double bonds in the chain, and examples thereof include a divalent group having a double bond formed by removing 2 to 5 hydrogen atoms of adjacent carbon atoms from the above alkylene group.

A preferred non-limiting specific example of the polymer unit having an electrophilic functional group at the end is a compound represented by the following formula (II) having four polyethylene glycol backbone branches and N-hydroxy-succinimidyl (NHS) groups at the ends.

[Chemical Formula 2]

(II)

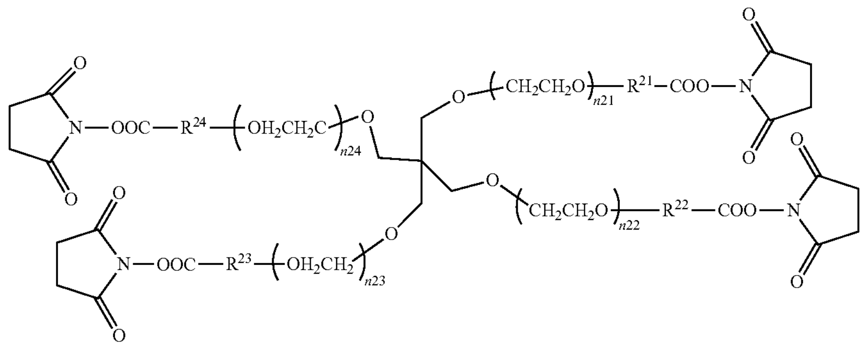

In the formula (II), $n_{21}$ to $n_{24}$ may be the same or different from each other. The closer the values of $n_{21}$ to $n_{24}$ are, the more homogeneous the network structure of the gel and the higher the strength, so the values are preferably closer, and more preferable the same. If the values of $n_{21}$ to $n_{24}$ are too high, the gel strength is weak, and when the values of $n_{21}$ to $n_{24}$ are too low, the gel is difficult to form due to steric hindrance of the compound. Therefore, examples of $n_{21}$ to $n_{24}$ include integer values of from 5 to 300, of which 20 to 250 is preferred, 30 to 180 is more preferred, 45 to 115 is still more preferred, and 45 to 55 is still more preferred. The weight average molecular weight (Mw) of the second four-branched compound of the present invention is from $1\times10^3$ to $1\times10^5$, preferably from $5\times10^3$ to $5\times10^4$, and more preferably from $1\times10^4$ to $4\times10^4$.

In the above formula (II), $R^{21}$ to $R^{24}$ are linker moieties connecting the functional groups and the core portion. $R^{21}$ to $R^{24}$ may be the same or different, but are preferably the same in order to produce a high-strength gel having a homogeneous network structure. In the formula (II), $R^{21}$ to $R^{24}$ are the same or different and each represent a $C_1$-$C_7$ alkylene group, a $C_2$ to $C_7$ alkenylene group, —NH—$R^{25}$—, —CO—$R^{25}$—, —$R^{26}$—O—$R^{27}$—, —$R^{26}$—NH—$R^{27}$—, —$R^{26}$—$CO_2$—, $R^{27}$—, —$R^{26}$—$CO_2$—NH—$R^{27}$—, —$R^{26}$—CO—$R^{27}$—, or —$R^{26}$—CO—NH—$R^{27}$—; wherein $R^{25}$ represents a $C_1$-$C_7$ alkylene group; $R^{26}$ represents a $C_1$-$C_3$ alkylene group; and $R^{27}$ represents a $C_1$-$C_5$ alkylene group.

In the present description, the alkylene and alkenylene groups may have one or more optional substituents. Examples of the substituent include, but are not limited to, alkoxy groups, halogen atoms (which may be fluorine, chlorine, bromine, or iodine atoms), amino groups, mono- or di-substituted amino groups, substituted silyl groups, acyl groups, and aryl groups. When the alkyl group has two or more substituents, they may be the same or different. The same applies to alkyl moieties of other substituents including alkyl moieties (for example, alkyloxy and aralkyl groups).

When a functional group is defined herein as "may have substituents", the type of the substituent, the substitution position, and the number of substituents are not particularly limited, and when it has two or more substituents, they may be the same or different. Examples of the substituent include, but are not limited to, alkyl groups, alkoxy groups, hydroxyl groups, carboxyl groups, halogen atoms, sulfo groups, amino groups, alkoxycarbonyl groups, and oxo groups. Further substituents may be present on these substituents.

As another aspect, a low molecular weight compound may be additionally used to crosslink the hydrophilic polymers. More specifically, one of the first or second polymer unit may be replaced by a low molecular weight compound. In this case, the low molecular weight compound has one or more nucleophilic or electrophilic functional groups in the molecule. This allows crosslinking and gelation between the second polymers by, for example, replacing the first polymer with a low-molecular weight compound having a nucleophilic functional group in the molecule and reacting it with a second polymer having one or more electrophilic functional groups on the side chain or at the end. Examples of the "low-molecular compound having a nucleophilic functional group in the molecule" include compounds having a thiol group in the molecule, such as dithiothreitol.

(1-2) Hydrogel

As described above, the gel material of the present invention includes a hydrogel (polymer gel) having a three-dimensional network structure formed by crosslinking of the hydrophilic polymers. The "gel" herein generally refers to a dispersion system of a polymer that has lost fluidity due to high viscosity, and satisfies G'≥G", wherein G' is storage modulus, and G" is loss modulus. The "hydrogel" is a gel containing water.

The hydrogel contained in the gel material of the present invention has a polymer content of from 1 to 5% by weight, preferably from 2 to 4% by weight. The hydrogel has an elastic modulus of from 100 to 10000 Pa, preferably from 500 to 5000 Pa. By setting the polymer content and the elastic modulus within appropriate ranges, it is possible to suppress undesirable effects such as excessive expansion of the gel when the area around the tendon or ligament is coated with the hydrogel, and also to make the gel have appropriate strength to remain in the affected area for a certain period of time.

The hydrogel contained in the gel material of the present invention preferably has an osmotic pressure of from 500 to 10000 Pa. In general, the osmotic pressure ($\pi_{OS}$) can be calculated by reverse osmosis of a sample prepared in a dialysis machine with polyvinyl pyrrolidone (PVP) solutions having different concentrations, and using the Flory-Rehner equilibrium equation shown below.

$$\pi_{OS}=\pi_{SW}+\pi_{el}=\pi_{PVP}+\pi_{el} \quad \text{[Mathematical formula 1]}$$

Here, $\pi_{SW}$ and $\pi_{el}$ represent the swelling pressure and elastic pressure of the target sample, respectively, and $\pi_{PVP}$ represents the osmotic pressure of the PVP solution.

2. Treatment Method and Others of the Present Invention

In another aspect, the present invention also relates to a method for treating an injured or ruptured tendon or ligament using the gel material. More specifically, it is a method to promote the healing of a tendon or ligament that needs to be treated due to injury or rupture by coating the affected area with the above gel material. Such coating of the affected area is typically performed after suture of a tendon or ligament.

By coating the tendon or ligament after suture with the gel material, entry of inflammatory cells and fibroblasts from around the affected area can be suppressed, and entry of scar tissue can be suppressed or eliminated. Surprisingly, the present invention has revealed that healing of a tendon or ligament proceeds efficiently even when scar tissue, which has been considered inevitable in the healing process of tendons and ligaments, is suppressed or eliminated.

The tendon or ligament to be treated herein is a tendon or ligament of a mammal selected from the group consisting of human, horse, pig, dog, cat, guinea pig, rabbit, rat, and mouse. It is typically a tendon or ligament in the human body.

As used herein, "injury or rupture" of a tendon or ligament may include traumatic injury or rupture (for example, by sports injuries, overuse, or medical or surgical intervention), injury due to genetic origin or disease, and disease. A "rupture" also includes a partial rupture.

As used herein, the "tendon" includes Achilles tendon, shoulder rotator cuff, hand and wrist tendons, patellar tendon, flexor tendon, and extensor tendon. Tendon "injuries" can include tendinosis, tendinitis, synovitis, tenosynovitis, and other injuries and tendon-related diseases such as avulsion.

As used herein, the "ligament" includes ligaments in the knee joint, shoulder, elbow, ankle joint, and spine. Examples of knee ligament "injuries" include lateral collateral ligament injuries, medial collateral ligament injuries, anterior cruciate ligament injuries, and posterior cruciate ligament injuries.

Although not necessarily bound by theory, as shown in the examples below, when the tendon or ligament is coated with the above gel material, the expression of type III collagen, which is characteristic of scar tissue, is significantly suppressed and the expression of type I collagen by the intratendinous cells is maintained, suggesting that the tendon or ligament is repaired by endogenous healing by the expression of the type I collagen. Such a healing process has not been elucidated previously, and is a mechanism that has been revealed for the first time by the present invention. Since about 95% of the collagen constituting the tendons is composed of type I collagen, this healing process is rational and ideal. This can be said to be the first effect achieved in the present invention in that healing occurs while the original function of the tendon or ligament is maintained.

Therefore, the method of the present invention can also be said to be a method for suppressing the expression of type III collagen in a tendon or ligament, including coating the area around the tendon or ligament after suture with the gel material. Alternatively, it can also be expressed that coating the area around the tendon or ligament after suture with the gel material can suppress the expression of type III collagen and maintain the expression of type I collagen.

As a typical aspect, the method for treating an injured or ruptured tendon or ligament of the present invention includes the steps of:

a) preparing a polymer solution A containing a first hydrophilic polymer having one or more nucleophilic functional groups on the side chain or at the end, and a polymer solution B containing a second hydrophilic polymer having one or more electrophilic functional groups on the side chain or at the end;

b) applying the polymer solutions A and B to the area around the tendon or ligament after suture to form a polymer gel having a three-dimensional network structure formed by crosslinking of the hydrophilic polymers, thereby coating the area around the tendon or ligament; and c) suppressing the expression of type III collagen in the tendon or ligament by the coating.

The type and the like of the hydrophilic polymers used in the steps a) and b) are as described above for the gel material of the present invention.

The solvent in the polymer solutions A and B is water, but in some cases, it may be a mixed solvent containing alcohols such as ethanol and other organic solvents. The polymer solutions A and B are preferably aqueous solutions with water as a sole solvent. The volumes of the polymer solutions A and B can be appropriately adjusted according to the area and complexity of the structure of the affected area to which they are applied, but are typically from 0.1 to 20 ml each, and preferably from 1 to 10 ml.

The pH of the polymer solutions A and B is typically from 4 to 8, and preferably from 5 to 7. The pH of polymer solutions A and B may be adjusted using pH buffers known in the art. For example, the pH can be adjusted to the above range by using a citric acid-phosphate buffer (CPB) and changing the mixing ratio of citric acid and disodium hydrogen phosphate.

In step b), the polymer solutions A and B may be applied independently to the area around the tendon or ligament, or a mixed solution of the polymer solutions A and B may be prepared immediately before application and then applied to the area around the tendon or ligament. This allows in-situ formation of the polymer gel (hydrogel).

The gelation time at that time is preferably from 10 to 300 seconds, and more preferably from 30 to 100 seconds. Again, the gelation time can be adjusted mainly by appropriately setting the polymer concentration, pH, and ionic strength in the polymer solution. Here, the "gelation time" is the time required for the storage modulus G' and the loss modulus G becomes G'=G".

The polymer gel formed around the tendon or ligament in step b) preferably remain around the affected area for the period necessary for the tendon or ligament to repair and regenerate. For example, the polymer gel has a decomposition rate of preferably from 10 to 90 days, more preferably from 20 to 50 days in vivo.

An example of a means for mixing the polymer solutions A and B is a two-component syringe as disclosed in International Publication WO2007/083522. The temperature of the two liquids at the time of mixing is not particularly limited, and may be any temperature at which the precursor units are each dissolved and the respective liquids are fluid. For example, the two liquids may be at different temperatures, but the same temperature is preferred for easier mixing.

Step c) is a step of coating the area around the tendon or ligament with a polymer gel to suppress the expression of type III collagen in the tendon or ligament. This is mainly based on the fact that the polymer gel coating around the tendon or ligament suppresses the entry of inflammatory cells and fibroblasts from around the area and suppresses or eliminates the entry of scar tissue in which type III collagen is rich. Although not necessarily bound by theory, it is believed that the treatment method of the present invention can suppress the expression of exogenous type III collagen based on the above scar tissue entry, while maintaining the expression of type I collagen by intratendinous cells, thereby causing endogenous healing.

In another aspect, the present invention also relates to a kit for preparing the gel material (polymer gel), which includes two or more solutions containing hydrophilic polymers. The kit is suitable for use in the above-described treatment method. The type of the hydrophilic polymers contained in the solutions are as described above, and those that can form hydrogels by crosslinking may be used. The solutions are preferably a polymer solution A containing a first hydrophilic polymer having one or more nucleophilic functional groups on the side chain or at the end and a polymer solution B containing a second hydrophilic polymer having one or more electrophilic functional groups on the side chain or at the end. Typically, the first and second hydrophilic polymers are polymers having a polyether or polyvinyl backbone, preferably bi-, tri- or tetra-branched polyethylene glycols.

The kit is suitable for use in the above-described treatment method. In that case, the kit may further include a medical instrument for covering the area around the tendon or ligament coated by the gel material. The medical instrument is suitable for stably fixing a tendon or ligament after suture, and is, for example, an instrument that can form a hollow cylindrical shape. However, an instrument having an appropriate shape may be used according to the position of the affected area, postoperative conditions, and the like.

EXAMPLES

The present invention will be described in more detail with reference to the following working examples, but these examples do not limit the present invention.

Example 1. Preparation of Polymer Solution

Tetrathiol-polyethylene glycol (Tetra-PEG-SH) having a —SH group at the end and tetramaleimidyl-polyethylene glycol (Tetra-PEG-MA) having a maleimidyl group at the end were used as the raw material polymers. These raw material polymers were each commercially available from NOF Corporation. Both have a molecular weight (molar mass) of 20,000. As a buffer for the polymer solution, sodium citrate buffer (pH 5.10; manufactured by FUJIFILM Wako Pure Chemical Corporation) was used.

The solution conditions used are as follows.

[Polymer Solution A]

Concentration: 2.5% by weight, Tetra-PEG-SH
pH: 5.10

[Polymer Solution B]

Concentration: 2.5% by weight, Tetra-PEG-MA
pH: 5.10

Example 2. Application to Rat Flexor Tendon Rupture Model

A rat model with a ruptured flexor tendon was created, and 25 μl of the polymer solution A and 25 μl of the polymer solution B were injected around the tendon after tendon suture, and gelation was confirmed after 90 seconds. The coating of the sutured affected tendon with the gel was found to block the entry of inflammatory cells and fibroblasts from the surrounding area without any problem. On the other hand, when not coated with the gel, the tendon was strongly covered with the scar tissue. FIG. 1 shows the images of the repair tendon coated with the gel of the present invention (gel group) and those not coated with the gel (control group).

Figure 2:
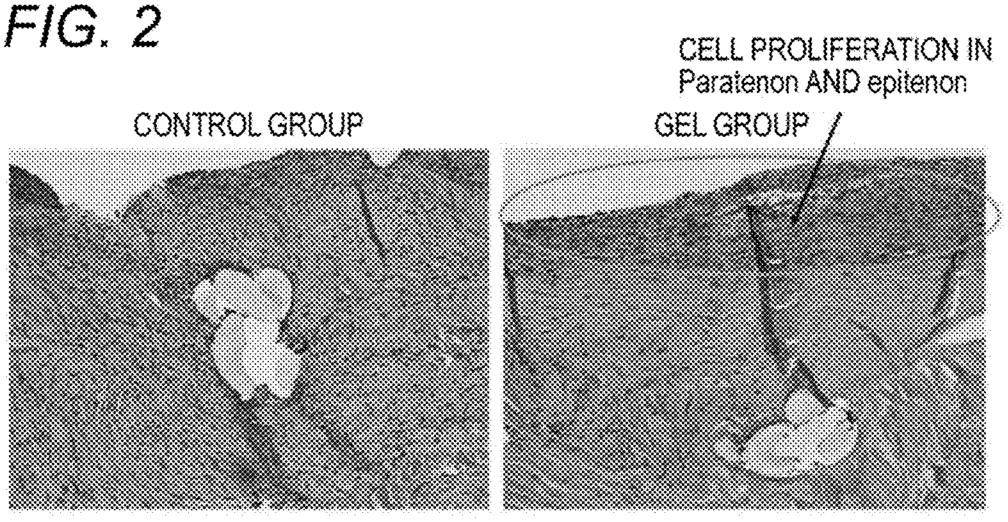
FIG. 2 shows images of tissue cross sections of a flexor tendon coated with the gel of the present invention (gel group) and a flexor tendon not coated with the gel (control group).

The repaired tendon coated with the gel of the present invention (gel group) and those not coated with the gel (control group) were evaluated histologically; on postoperative day 21, the gel group showed strong cell proliferation along the long axis of the tendon in tissues within the tendon such as epitenon and paratenon, whereas the control group showed a strong presence of disordered abnormal proliferation of fibroblasts and neovascularization around the tendon (FIG. 2). This suggested that in the gel group, precursor cells present in the tendon were mainly involved in the healing process.

Furthermore, a comparative analysis of the expressed genes in the healing process of both groups was performed using tendon tissue from organ culture; in the control group, Col3a1 (type III collagen), which is characteristic of scar tissue, was strongly expressed early postoperatively, whereas in the gel group, Col3a1 was expressed only in small amounts and Col1a1 (type 1 collagen) was strongly expressed from 2 to 3 weeks after surgery. From the above, it was found that in the control group, healing of scar tissue occurs early in the healing process with type III collagen as the main component, whereas in the gel group, healing with type III collagen by intratendinous cells occurs.

The invention claimed is:

1. A method for treating an injured or ruptured tendon or ligament, comprising coating an area around the tendon or ligament after suture with, a gel material comprising a polymer gel;

wherein the polymer gel is a hydrogel having a three-dimensional network structure formed by crosslinking of hydrophilic polymers;

wherein the hydrophilic polymers comprise a first hydrophilic polymer having one or more nucleophilic functional groups on a side chain or at an end and a second hydrophilic polymer having one or more electrophilic functional groups on a side chain or at an end;

wherein the first hydrophilic polymer and the second hydrophilic polymer are tetra-branched polyethylene glycol;

wherein the polymer gel has a polymer content of from 1 to 5% by weight and an elastic modulus of from 100 to 10000 Pa; and wherein the one or more nucleophilic functional groups are selected from the group consisting of a thiol group and an amino group, and the one or more electrophilic functional groups are selected from the group consisting of a maleimidyl group, an N-hydroxy-succinimidyl (NHS) group, a sulfosuccinimidyl group, a phthalimidyl group, an imidazoyl group, an acryloyl group, a nitrophenyl group, an isothiocyanate group, an aldehyde group, an iodoacetamide group, a vinyl sulfone group, and —$CO_2PhNO_2$; and suppressing expression of type III collagen in the tendon or ligament by the coating while maintaining expression of type I collagen, and suppressing expression of type III collagen in the tendon or ligament by the coating while maintaining expression of type I collagen.

2. A method for suppressing expression of type III collagen in a tendon or ligament, comprising coating an area around the tendon or ligament after suture with a gel material comprising a polymer gel;

wherein the polymer gel is a hydrogel having a three-dimensional network structure formed by crosslinking of hydrophilic polymers;

wherein the hydrophilic polymers comprise a first hydrophilic polymer having one or more nucleophilic functional groups on a side chain or at an end and a second hydrophilic polymer having one or more electrophilic functional groups on a side chain or at an end;

wherein the first hydrophilic polymer and the second hydrophilic polymer are tetra-branched polyethylene glycol;

wherein the polymer gel has a polymer content of from 1 to 5% by weight and an elastic modulus of from 100 to 10000 Pa; and wherein the one or more nucleophilic functional groups are selected from the group consisting of a thiol group and an amino group, and the one or more electrophilic functional groups are selected from the group consisting of a maleimidyl group, an N-hydroxy-succinimidyl (NHS) group, a sulfosuccinimidyl group, a phthalimidyl group, an imidazoyl group, an acryloyl group, a nitrophenyl group, an isothiocyanate group, an aldehyde group, an iodoacetamide group, a vinyl sulfone group, and —$CO_2PhNO_2$; and suppressing expression of type III collagen in the tendon or ligament by the coating while maintaining expression of type I collagen.

3. A method for treating an injured or ruptured tendon or ligament, comprising steps of:

applying polymer solutions A and B to an area around the tendon or ligament after suture to form a polymer gel having a three-dimensional network structure formed by crosslinking of hydrophilic polymers, thereby coating the area around the tendon or ligament; and suppressing expression of type III collagen in the tendon or ligament by the coating while maintaining expression of type I collagen, wherein the polymer solution A contains a first hydrophilic polymer having one or more nucleophilic functional groups on a side chain or at an end, and the polymer solution B containing a second hydrophilic polymer having one or more electrophilic functional groups on a side chain or at an end, wherein the first hydrophilic polymer and the second polymer are tetra-branched polyethylene glycol, and wherein the polymer gel has a polymer content of from 1 to 5% by weight and an elastic modulus of from 100 to 10000 Pa and wherein the one or more nucleophilic functional groups are selected from the group consisting of a thiol group and an amino group, and the one or more electrophilic functional groups are elected from the group consisting of a maleimidyl group, an N-hydroxy-succinimidyl (NHS) group, a sulfosuccinimidyl group, a phthalimidyl group, an imidazoyl group, an acryloyl group, a nitrophenyl group, an isothiocyanate group, an aldehyde group, an iodoacetamide group, a vinyl sulfone group, and —$CO_2PhNO_2$.

* * * * *